US010842408B2

(12) United States Patent
Duek (10) Patent No.: US 10,842,408 B2
(45) Date of Patent: Nov. 24, 2020

(54) POSITION DETECTORS FOR IN-VIVO DEVICES AND METHODS OF CONTROLLING SAME

(71) Applicant: DiamSense Ltd., Ramat Gan (IL)

(72) Inventor: Dotan Duek, Ramat-Gan (IL)

(73) Assignee: DIAMTECH LTD., Ramat-Gan (IL)

( * ) Notice: Subject to any disclaimer, the term of this patent is extended or adjusted under 35 U.S.C. 154(b) by 88 days.

(21) Appl. No.: 16/055,284

(22) Filed: Aug. 6, 2018

(65) Prior Publication Data

US 2019/0038177 A1 Feb. 7, 2019

Related U.S. Application Data

(60) Provisional application No. 62/541,788, filed on Aug. 7, 2017.

(51) Int. Cl.
*A61B 5/06* (2006.01)
*A61B 5/00* (2006.01)
*A61B 34/20* (2016.01)
*A61B 1/00* (2006.01)

(52) U.S. Cl.
CPC ............ *A61B 5/061* (2013.01); *A61B 5/0071* (2013.01); *A61B 5/0084* (2013.01); *A61B 5/06* (2013.01); *A61B 34/20* (2016.02); *A61B 1/00016* (2013.01); *A61B 2034/2051* (2016.02)

(58) Field of Classification Search
CPC ...................................... A61B 5/061
USPC .......................................... 356/614
See application file for complete search history.

(56) References Cited

U.S. PATENT DOCUMENTS

| 2011/0166442 | A1 | 7/2011 | Sarvazyan | |
| 2015/0238125 | A1* | 8/2015 | Acosta | A61B 5/0075 600/310 |
| 2015/0374250 | A1* | 12/2015 | Hatano | A61B 5/04008 600/409 |
| 2016/0161429 | A1 | 6/2016 | Englund et al. | |
| 2016/0356863 | A1* | 12/2016 | Boesch | G01R 33/032 |

(Continued)

OTHER PUBLICATIONS

European Search Report of Application No. EP 18187553 dated Dec. 13, 2018.

*Primary Examiner* — Tarifur R Chowdhury
*Assistant Examiner* — Omar H Nixon
(74) *Attorney, Agent, or Firm* — Pearl Cohen Zedek Latzer Baratz LLP (57) ABSTRACT

The position detector disclosed may include: a diamond with nitrogen vacancy centers; an activator configured to activate the nitrogen vacancy centers in the diamond to emit fluorescence signals; a sensor configured to detect the fluorescence signals emitted from the diamond, and a controller configured to control components of the position detector. The controller may be configured to: control the activator to activate the nitrogen vacancy centers in the diamond; control a first EM radiation source to generate one or more EM signals; receive via the sensor one or more first indications of one or more first fluorescence signals; control a second EM radiation source to generate one or more EM signals; receive via the sensor one or more second indications of one or more second fluorescence signals; and calculate the position of the diamond based on the received indications. The position detector has utility in detecting a medical tool in the body of a subject, for example.

19 Claims, 4 Drawing Sheets

(56) References Cited

U.S. PATENT DOCUMENTS

| | | |
|---|---|---|
| 2017/0010594 A1 | 1/2017 | Kottapalli et al. |
| 2017/0176577 A1 | 6/2017 | Halliday |
| 2017/0234941 A1* | 8/2017 | Hatano .............. G01R 33/1284 324/304 |
| 2017/0328965 A1* | 11/2017 | Hruby .................... G01R 33/60 |
| 2017/0343695 A1* | 11/2017 | Stetson .................. G01V 3/101 |

* cited by examiner

POSITION DETECTORS FOR IN-VIVO DEVICES AND METHODS OF CONTROLLING SAME

CROSS REFERENCE TO RELATED APPLICATIONS

This application claims the benefit of U.S. Provisional Patent Application Ser. No. 62/541,788, filed on Aug. 7, 2017, and entitled POSITION DETECTORS FOR MEDICAL DEVICES AND METHODS OF CONTROLLING SAME, which is incorporated herein by reference in its entirety.

TECHNICAL FILED OF THE INVENTION

The invention generally relates to a device and a method for detection of an in-vivo location of a device in a body of a subject and more particularly, a device and method for detection an in-vivo location of a device in a body of a subject using diamonds having nitrogen vacancy centers.

BACKGROUND OF THE INVENTION

In the world of in-vivo medical procedures, minimally invasive surgical procedures and other procedures involving in-vivo sensing, physicians and surgeons typically suffer from limited knowledge regarding the location of the medical tool. Some medical tools include small cameras that present images from the close environment around the medical tool. However, the location of the tool inside the body during both the insertion of the tool and the operation itself, is usually determined by an external detector, such as ultrasound transducer, X-ray imager and the like. These external detectors may emit harmful radiation (e.g., X-ray) and therefore cannot be operated for long periods of time, or they may require full contact with the subject's body (e.g., ultrasound transducer), thus interrupting the medical procedure.

Therefore, there is a need for methods and devices adapted to detect the location of a medical tool, such as a catheter, inside the subject's body, using harmless radiation and operated in ways that will not disturb the medical procedure.

SUMMARY OF THE INVENTION

Aspects of the invention may be directed to a position detector for in-vivo devices. The positioning detector may include: a diamond with nitrogen vacancy centers; an activator configured to activate the nitrogen vacancy centers in the diamond to emit fluorescence signals; a sensor configured to detect the fluorescence signals emitted from the diamond, and a controller configured to control components of the position detector. In some embodiments, the sensor may include a light guide connected to the diamond, and the light guide may be configured to transmit the fluorescence signals from the diamond to a light detector. In some embodiments, the sensor may include two electrodes placed at opposite sides of the diamond.

In some embodiments, the two or more EM radiation sources may generate EM signals at a frequency range of 1-100 KHz. In some embodiments, the EM radiation sources may generate Direct Current (DC) or Alternating Current (AC) EM signals. In some embodiments, the diamond may include between 1 ppb-5000 ppm of nitrogen vacancy centers. In some embodiments, the diamond and the sensor may be attached to the in-vivo device in order to determine an in-vivo location of at least a portion of the medical device. In some embodiments, the diamond may be placed no more than 300 cm from the location of each of the EM radiation sources.

In some embodiments, the controller may be configured to execute methods and instructions as disclosed herein. The controller may be configured to: control the activator to activate the nitrogen vacancy centers in the diamond; control a first EM radiation source of the two or more EM radiation sources to generate one or more EM signals; receive via the sensor one or more first indications of one or more first fluorescence signals; control a second EM radiation source of the two or more EM radiation sources to generate one or more EM signals; receive via the sensor one or more second indications of one or more second fluorescence signals; and calculate the position of the diamond based on the received indications.

In some embodiments, the positioning detector may further include a third radiation source located in a third fixed location and the controller may be configured to: generate one or more EM signals from the third EM radiation source; receive via the sensor one or more third indications of one or more third fluorescence signals in the diamond; and calculate the position of the diamond further based on the received one or more third indications.

In some embodiments, the controller may be configured to: control the activator to emit microwave radiation at at least three predefined frequencies, each is configured to activate nitrogen vacancy centers at a known crystallographic direction; generate one or more EM signals from the first EM radiation source; receive via the sensor at least three first indications of at least three first fluorescence signals in the diamond, each first fluorescence signal corresponds to light emitted due to the activation of nitrogen vacancy centers at the known crystallographic direction; generate one or more EM signals from the second EM radiation source; and receive via the sensor at least three second indications of at least three second fluorescence signals in the diamond, each second fluorescence signal corresponds to light emitted due to the activation of nitrogen vacancy centers at the known crystallographic direction. In some embodiments, calculating the position of the diamond may include determining a first vector extending between the diamond and the first EM radiation source based on the at least three first indications and the location of the first EM radiation source; determining a second vector extending between the diamond and the second EM radiation source based on the at least three second indications and the location of the second EM radiation source; and calculating the position of the diamond as the intersection point of the first and second vectors.

In some embodiments, calculating the position of the diamond may include: calculating a first distance between the diamond and the first EM radiation source based on a time duration between the generation of the first EM signal and the first fluorescence signal; and calculating a second distance between the diamond and the second EM radiation source based on a time duration between the generation of the second EM signal and the second fluorescence signal.

In some embodiments, calculating the position of the diamond may include: receiving measurements of a first fluorescence intensity of the first the first fluorescence signal and a second fluorescence intensity of the second fluorescence signal; calculating a first distance between the diamond and the first EM radiation source based on the first fluorescence intensity; and calculating a second distance between the diamond and the second EM radiation source based on the second fluorescence intensity.

In some embodiments, the controller may further be configured to: receive a first fluorescence signal and a second fluorescence signal when the diamond is in a first position; receive a first fluorescence signal and a second fluorescence signal when the diamond is in a second position; calculate a first phase shift between the first fluorescence signals received at when diamond is in the first and second positions; and calculate a second phase shift between the second fluorescence signals received at when diamond is in the first and second positions. In some embodiments, calculating the position of the diamond may include: calculating a first distance based on the first phase shift and a second distance based on the second phase shift.

In some embodiments, the controller may further be configured to calibrate the position detector by: placing the EM radiation sources in known distances from the diamond; generating EM signals from each EM radiation source; measuring time differences between the generation of each EM signal and a corresponding fluoresces signal; and correlating between known distances and the time differences.

In some embodiments, the controller may further be configured to calibrate the position detector by: placing the EM radiation sources in known distances from the diamond; generating EM signals from each EM radiation source; measuring an intensity of a fluorescence signal for each EM signals; and associating the intensity of a fluorescence signal with a known distance.

In some embodiments, the controller may further be configured to calibrate the position detector by: placing the first EM radiation source in a first known distance and the second EM radiation source in a second known distance from the diamond; generating a first EM signal form the first EM radiation source and a second EM signal form the second EM source; placing the first EM radiation source in a third known distance and the second EM radiation source in a fourth known distance from the diamond; generating a third EM signal form the first EM radiation source and a fourth EM signal form the second EM source; calculating a first phase shift between the first and third fluorescence signals; calculating a second phase shift between the second and fourth fluorescence signals; correlating between the first phase shift and a change between the first and third distances; and correlating between the second phase shift and a change between the second and fourth distances.

Some additional aspects of the invention may be related to a position detector for in-vivo devices. In some embodiments, the position detector may include: two diamonds with nitrogen vacancy centers located at a known distance from each other; at least one sensor for detecting fluorescence signals from the two diamonds; at least one activator for activating the nitrogen vacancy centers in the two diamonds; one electromagnetic (EM) radiation source located in a fixed location; and a controller configured to control various components of the position detector.

In some embodiments, the controller may be configured to: control the activator to emit microwave radiation at at least three predefined frequencies, each frequency selected to activate nitrogen vacancy centers at a known crystallographic direction; generate one or more EM signals from the EM radiation source; receive, via the at least one sensor, at least three first indications of at least three first fluorescence signals in a first diamond of the two diamonds, each first fluorescence signal corresponding to light emitted due to the activation of nitrogen vacancy centers at the known crystallographic direction; receive, via the at least one sensor, at least three second indications of at least three second fluorescence signals in a second diamond of the two diamonds, each second fluorescence signal corresponding to light emitted due to the activation of nitrogen vacancy centers at the known crystallographic direction; determine a first vector extending between the first diamond and the EM source based on the at least three first indications, and the location of the EM source; determine a second vector extending between the second diamond and the EM source based on the at least three second indications and the location of the EM source; and calculate the location of the first and second diamonds based on the first and second vectors and the distance between the first and second diamonds.

In some embodiments, the at least one sensor may include a light guide connected to the diamond, to pass optical signals from the diamond. In some embodiments, the at least one sensor may include two electrodes placed from opposite sides of the diamond. In some embodiments, the EM radiation source may generate EM signals at 1-100 KHz. In some embodiments, the EM radiation source may generate Direct Current (DC) or Alternating Current (AC) EM signals. In some embodiments, each diamond from the two diamonds may include between 1 ppb-5000 ppm of nitrogen vacancy centers. In some embodiments, the two diamonds and the sensor may be attached to a medical device in order to determine the in-vivo location of at least a portion of the medical device. In some embodiments, the EM radiation source is located at no more than 300 cm from each diamond.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Some aspects of the invention may include a positioning detector for in-vivo devices based on a diamond having nitrogen vacancy (NV) centers. An NV center is an artificial crystal defect introduced into the diamond's crystal structure in order to fluoresce (emit visible light) upon excitation. An NV center may be made, for example, by irradiating the diamond with electromagnetic energy. The excitation can be transferred using a light-guide (e.g., an optical fiber) and detected by a light detector. Accordingly, at least one diamond having NV centers attached to the tip of an in-vivo medical device, such as a catheter, may allow detection of the location of the medical device in the subject's body upon detecting a fluorescence signal.

In some embodiments, an NVC diamond located in the subject's body may be irradiated with AC or DC pulses of Electro Magnetic (EM) energy, for example, at 1-100 KHz (which is considered non-ionizing radiation) from at least two (e.g., three) EM radiation sources located at known positions around the subject. For example, when a two dimensional upper view of the procedure is sufficient for controlling the medical device, two EM sources may be sufficient to receive a reliable location of the medical tool. In such case, two EM sources may be located at fixed positions at a plane comprising the subject (e.g., the plane of the operating table) and emitting EM waves in directions perpendicular to each other. In other examples, three EM sources located in fixed locations may be used in order to find the location of the in-vivo device (e.g., a medical tool) in three-dimensions, using triangulation. The EM pulses may penetrate through the subjects' body tissues and interact with the NV centers in the diamond. Following the emission of an EM pulse (e.g., signals) from a first EM source, a first fluorescence signal in the diamond may be detected. The distance between the first EM source and the diamond may be calculated using, for example, the time duration between the emission of the first EM pulse and the detection of the first fluorescence signal, as will be discussed below with respect to FIG. 2. Calculating the distance of the diamond from three different EM sources placed in known locations may allow calculation of the exact position of the diamond, and thus, the tip of the medical tool in respect to the two or more EM sources. In some embodiments, in order to find the location of the diamond and the device in the subject's body, a calibration process may be performed that correlates the location of the diamond with respect to the EM sources and the actual location of the diamond with respect to the subject's body. The calibration process may include taking an image of the diamond, whether in the subject's body or not, by one or more additional imagers such as MRI, CT and the like. The imager may either be located in a known location with respect to the EM sources or the image taken may include the EM sources and a scale. Accordingly, the location of the diamond in a 3D image taken by the imager may be correlated to a calculated location of the diamond, according to some embodiments of the invention. In some embodiments, at the beginning of an operation procedure, an image of the subject and/or an image of the organ being operated on may be taken by the imager Additionally or alternatively, a 3D model of the organ may be simulated using images taken by the imager. Simultaneously, an image of the diamond may be taken by the imager and merged with a calculated location of the diamond in the organ. From that point onward, the calculated location of the diamond may be incorporated into the image of the organ or 3D model and presented (e.g., as an animated mark) on a screen, to a user conducting the medical procedure. Following the progress of the diamond and the medical tool the animated mark may be shown on the screen. In some embodiments, updated images or 3D models of the organ may be taken and/or simulated periodically during the medical procedure.

Some additional aspects of the invention may include using a position detector that includes two diamonds each having NV centers located at a known distance from each other, for example, a long a catheter or from two sides of the catheter. In some embodiments, the detector may further include at least one activator for activating the NV centers in the two diamonds, at least one sensor for detecting fluorescence signals from the two diamonds and one or a plurality of electromagnetic (EM) radiation sources located in a known location. The position of the two diamonds may calculated according to a method disclosed in FIG. 3.

Figure 1A:
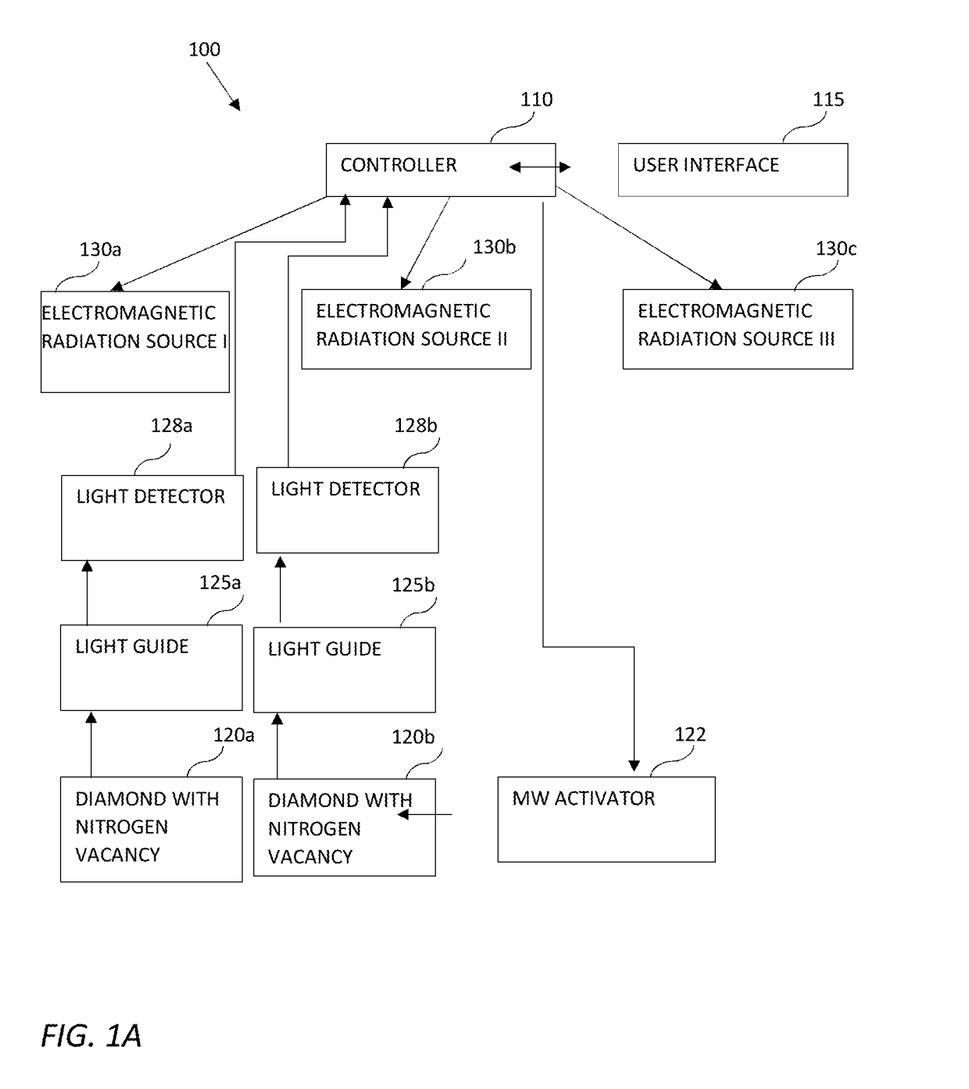
FIG. 1A is high level block diagram of a position detector for in-vivo devices according to some embodiments of the invention.

Reference is now made to FIG. 1A which is a high-level block diagram of a position detector for medical devices according to some embodiments of the invention. A position detector 100 may include one or more diamonds 120a and/or 120b with nitrogen vacancy centers (NVC), one or more sensors 128a and/or 128b connected to diamond 120a or diamond 120b respectively by way of light guides 125a or 125b, two or more (e.g., three) electromagnetic (EM) radiation sources 130a-130c located in fixed (i.e., known) locations, and a controller 110.

Diamond 120a and/or diamond 120b may have a plurality of NV centers, for example, between 1 ppb-5000 ppm. The higher the amount of NV centers the stronger the fluorescence signal following multiple fluorescence signals that may occur simultaneously. Diamond 120a and/or diamond 120b may be connected to the tip of a medical device, e.g., a catheter, a laparoscope, an endoscope, and the like. In some embodiments, system 100 may further include an activator 122 (e.g., a microwave activator or any other activator) for activating the NV centers in diamond 120. Activator 122 may include an antenna located in proximity to diamond 120a and/or 120b. Upon emitting MW radiation, e.g., at 2.8-2.84 GHz, in proximity to the diamond, the NV centers in the diamond may generate visual light photons to form a fluorescence signal. Any additional EM radiation reaching diamond 120a and/or 120b may cause further fluorescence. At least some of the fluorescent photons may be transmitted by a light-guide 125a or 125b (which may be included in sensor 128a or 128b) and detected by detector/sensor 128a or 128b. In some embodiments, controller 110 may control MW activator 122 to activate the NV centers in diamond 120.

Sensor 128a and/or sensor 128b may be any device that may be configured to detect fluorescence signals from diamond 120. For example, sensor 128a and/or sensor 128b may include a light-guide 125a and/or 125b, such as an optical fiber, connected to the diamond. The optical fiber may further be attached to the medical device and may follow the path of the medical device in the subject's body. The light-guide may pass the fluorescence signal to a light detector 128 (e.g., a camera) and controller 110. In some embodiments, sensor 128a and or sensor 128b may include two electrodes located on opposite sides of diamond 120a or diamond 120b respectively and configured to sense changes in an electrical field caused by a fluorescence signal. The two electrodes may be connected to a conducting line and further be attached to the medical device and may follow the path of the medical device in the subject's body.

EM sources 130a-130c may be any EM source (e.g., an antenna and EM generator) that is configured to generate and emit EM pulses or signals. EM sources 130a-130c may emit AC or DC EM radiation, for example, at 1-100 KHz. It should be appreciated that the EM source may be any non-ionizing radiation source, such as, for example, a source emitting EM radiation at a wavelength of 1 mm. In some embodiments, at least one of: the phase, the frequency and the intensity of the EM pulses generated by each one of EM sources 130a-130c may be predetermined and controlled, for example, by controller 110. In some embodiments, two or more electromagnetic (EM) radiation sources 130a-130b may be located in fixed (i.e., known) locations, for example, at fixed locations at an operation room (or any other room) at which positioning detector 100 is located. In some embodiments, a third radiation source 130c located in a third fixed location, as illustrated in FIG. 1B may be included in detector 100.

In some embodiments, the fluorescence signals generated by diamond 120a and/or diamond 120b may follow the pattern of the EM radiation applied by EM sources 130a-130c. For example, if an AC wave of EM radiation at 50 KHz is generated from EM source 130b a corresponding 50 KHz fluorescence signal may be received from diamond 120a and/or diamond 120b and detected by detector 128a and/or diamond 128b. Furthermore, the intensity of the exited fluorescence signal may be proportional, for example, linearly proportional to the intensity of the EM signal reaching diamond 120a and/or diamond 120b. The higher the intensity of the EM signal the higher the intensity of the exited fluorescence signal.

Figure 1B:
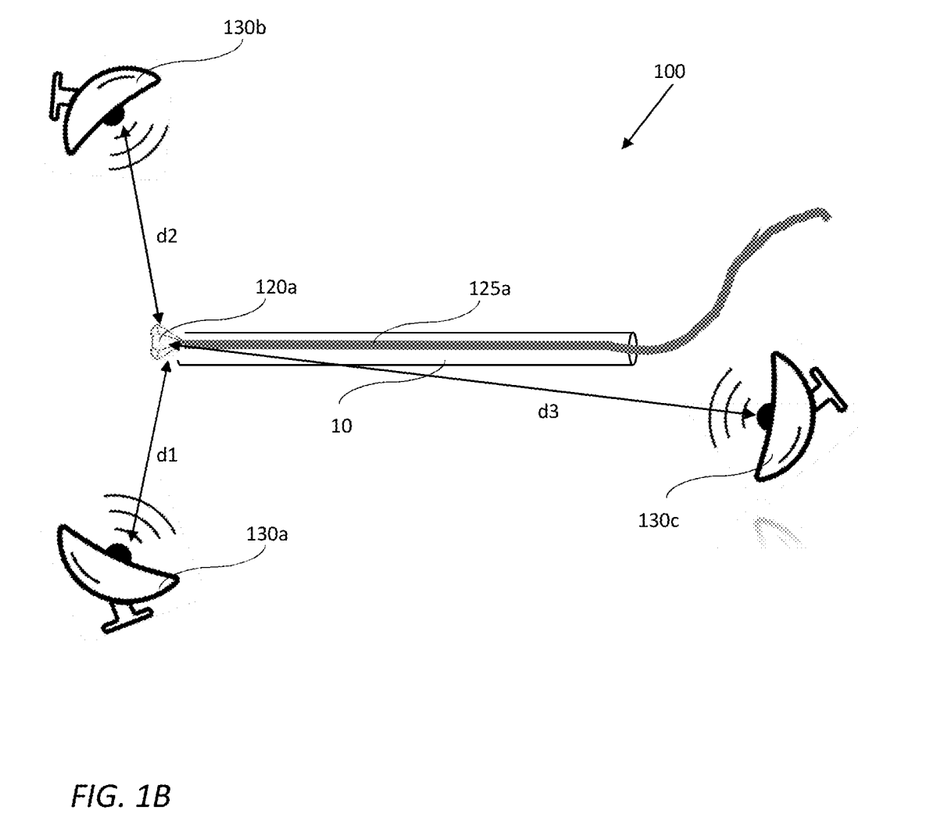
FIG. 1B is an illustration of a position detector and an in-vivo device according to some embodiments of the invention.

FIG. 1B is an illustration of some of the components of position detector for in-vivo device 100 according to some embodiments of the invention. Diamond 120a may be located at the tip of an in-vivo device 10, for example, a catheter and connected to a sensor 128a attached along medical in-vivo device 10. Diamond 120a and sensor 128a may follow the movement of the tip of medical device 10. EM sources 130a-130c may be located in fixed location in space, for example, at known locations in a room accommodating positioning detector 100. In some embodiments, diamond 120a may be placed at less than 300 cm from each of EM sources 130a-130c. Accordingly, d1, d2 and d3 may all be less than 300 cm. The coordinates of the fixed locations of EM sources 130a-130c may be uploaded to a memory associated with controller 110. In some embodiments, these coordinates may be used in calculating the position of diamond 120a.

Figure 1C:
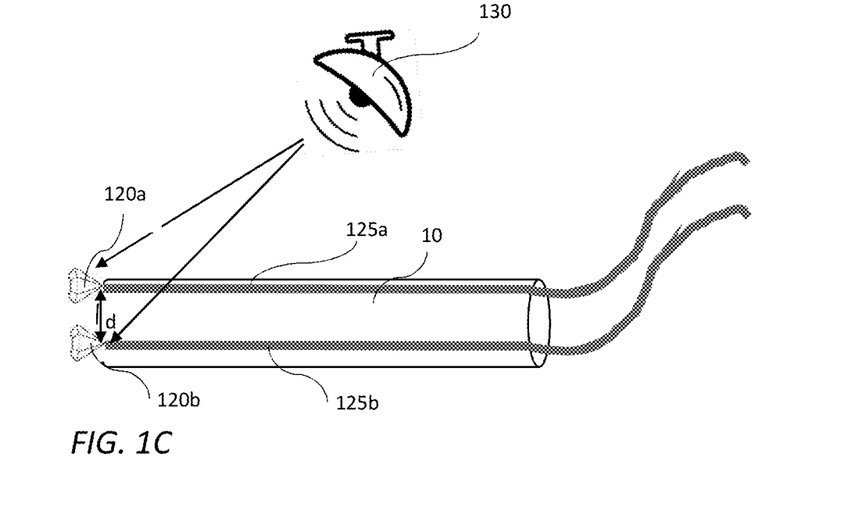
FIG. 1C is an illustration of another position detector and an in-vivo device according to some embodiments of the invention.

FIG. 1C is an illustration of some of the components of another position detector 100 according to some embodiments of the invention. Position detector 100 may include two diamonds 120a and 120b located at known distance d from each other and one EM source 130 located at a fixed (i.e., known) location, for example, at a fixed placed in an operation room accommodating positioning detector 100. The coordinates of the fixed location of EM source 130 may be uploaded to a memory associated with controller 110.

Controller 110 may be any computation device that is configured to store and execute methods and instructions according to some embodiments of the invention. Controller 110 may include a processor that may be for example, a chip and a memory. The memory may include any non-volatile memory that may store any executable codes, e.g., an application, a program, a process, task or script. The executable code may include codes for controlling a position detector or any other codes or instruction for executing methods according to embodiments of the present invention. The executable code may be executed by the processor. Controller 110 may further include any operating system that may be or may include any code segment designed and/or configured to perform tasks involving coordination, scheduling, arbitration, supervising, controlling or otherwise managing the operation of controller 110. In some embodiments, controller 110 may be a cloud-based computing service that may include a cloud-based storage service.

Controller 110 may include or may be in communication with a user interface 115. User interface 115 may include any input and output devices that may allow controller 110 to receive instructions from a user and display outputs for the user. For example, user interface 115 may include a keyboard, a screen, a touch screen, a mouse, or the like, that may allow a user to upload codes and instructions. In some embodiments, user interface 115 may include a screen placed in the field of view of the physician operating on the subject, showing him/her the location of the diamond in real time, as will be discussed below with respect to FIG. 2. It will be recognized that any suitable number of output devices may be included in user interface 115. Any applicable input/output (I/O) devices may be connected to controller 110. For example, a wired or wireless network interface card (NIC), a modem, printer or facsimile machine, a universal serial bus (USB) device or external hard drive may be included in user interface 115.

Figure 2:
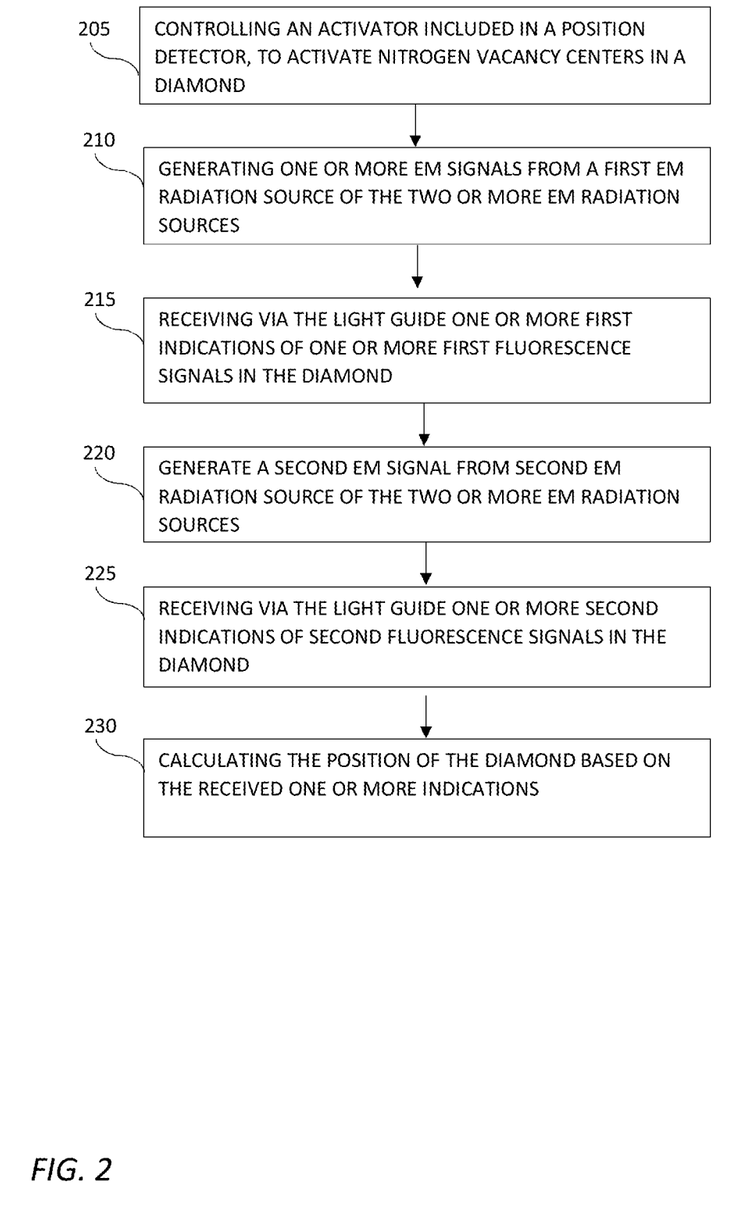
FIG. 2 is a flowchart of a method of controlling a position detector for in-vivo devices according to some embodiments of the invention.

Reference is now made to FIG. 2 which is a flowchart of a method of controlling a position detector for medical devices according to some embodiments of the invention. The method of FIG. 2 may be performed by controller 110 of system 100 or by any other suitable controller. In some embodiments, the controller may control the activator to activate the nitrogen vacancy centers in the diamond, in step 205. For example, activator 122 may emit MW radiation, e.g., at 2.8-2.84 GHz, in proximity to the diamond causing the NV centers in diamond 120a to generate visual light photons to form a fluorescence signal.

In some embodiments, activator 122 may be controlled to emit microwave radiation at at least three predefined frequencies, each is configured to activate NV centers at a known crystallographic direction in the diamond crystal. For example, a first MW frequency may activate NV centers in the <111> crystallographic direction, a second MW frequency may activate NV centers in the <1-11> crystallographic direction, a third MW frequency may activate NV centers in the <11-1> crystallographic direction and a fourth MW frequency may activate NV centers in the <-111> crystallographic direction.

In some embodiments, the controller may generate one or more first EM signals from a first EM radiation source of the two or more EM radiation sources, in step 210. For example, an EM pulse of 50 KHz may be generated from EM source 130a and transmitted towards diamond 120a. The location of EM source 130a in space (e.g., the coordinates with respect to a fixed point in the room accommodating detector 100) may be known and stored in a storage unit associated with the controller, for example, a memory associated with controller 110. In some embodiments, the intensity, the frequency and/or the phase of the first EM signal may be predetermined and adjusted (e.g., by controller 110) prior to the generation of the first EM signal.

In some embodiments, the controller may receive via the sensor one or more first indications of a first fluorescence signal in the diamond, in step 215. Being exposed to the first EM signal at least one NV center in diamond 120a may excite EM radiation in a typical (single) EM wavelength (e.g., in the visual light spectrum) corresponding to the energy gap formed by the NV centers. This excitation of EM energy may be detected by sensor 128*a*.

In some embodiments, when activator 122 emits microwave radiation at at least three predefined frequencies, the controller may be configured to receive via sensor 128 at least three first indications of at least three first fluorescence signals in diamond 120*a*, each first fluorescence signal corresponds to light emitted due to the activation of NV centers at the corresponding crystallographic direction.

In some embodiments, the controller may generate one or more second EM signals from a second EM radiation source of the two or more EM radiation sources, in step 220. In a similar way to the first EM signal, the second EM signal may be generated from EM source 130*b* and controller 110 may control the frequency, phase and/or intensity of the second EM signal. In some embodiments, the controller may receive via the sensor one or more second indications of one or more second fluorescence signal in the diamond, in step 225. Upon being exposed to the second EM signal the NV centers in diamond 120*a* may excite EM radiation in a typical (single) EM wavelength (e.g., in the visual light spectrum) corresponding to the energy gap formed by the NV centers. This excitation of EM energy may be detected by sensor 128 as the second fluorescence signal.

In some embodiments, when activator 122 emits microwave radiation at at least three predefined frequencies, the controller may be configured to receive via the sensor at least three second indications of at least three second fluorescence signals in diamond 120*a*, each second fluorescence signal may correspond to light emitted due to the activation of NV centers at the known crystallographic direction.

In some embodiments, a third EM signal may be generated from a third EM source (e.g., EM source 130*c*) and a third one or more fluorescence signals may be detected by the controller.

In some embodiments, the controller may be configured to calculate the position of the diamond based on the received indications, in step 330, as will be discussed below. In some embodiments, the controller may calculate the position of the diamond based on the received first, second and/or third indications.

In some embodiments, calculating the position of the diamond may include calculating a first distance between the diamond and the first EM radiation source. In order to correlate between the fluorescence signal and the distance between the EM sources and diamond 120*a*, system 100 may undergo a calibration process. Diamond 120 may be placed in a known location in space at known distances d1, d2 and d3 (illustrated in FIG. 1B) from EM sources 130*a*-130*c*.

According to some embodiments, the calibration process may include measuring the time differences t1, t2 and t3 between the generation of EM signal in each EM source and the excitation of the corresponding fluorescence signal in the diamond. Accordingly, a correlation may be set between the known distances d1, d2 and d3 and the corresponding time differences t1, t2 and t3.

According to some embodiments, the distances between the EM sources and the diamond may be calculated according to the Signal Intensity Method. EM waves (except for resonant waves) decay in intensity as they progress through space. Furthermore, since the intensity of the excitation of the fluorescence signal is directly proportional to the intensity of the EM wave reaching the diamond, it is possible to correlate between the distances of the EM source from the diamond and the intensity of the fluorescence signal. As the distance between diamond 120*a* (and in-vivo device 10) and the EM sources increases, the intensity of the fluorescence signal may decline proportionally. Therefore, a calibration process using the Signal Intensity Method may associate the distance between each EM source and the diamond, and the intensity of fluorescence signal received from an excitation following the generation of an EM signal from each EM source.

Another example for such method may be the Phase Shift Calculation Method. A phase shift in the fluorescence signal may occur due to the movement of diamond 120*a* from one point to another with respect to EM sources 130*a*-130*c*. The measured phase shift may be correlated to the change in distance. For such a method, from each EM source an AC EM radiation may be generated when the diamond is placed in first known distances ($d_1^{st}$, $d_2^{st}$ and $d_3^{st}$) from each EM sources. Three first fluorescence signal, one for each EM source, may be received in sensor 128*a* and recorded by controller 110. Diamond 120*a* may be shifted to a second known position having second known distances ($d_1^{nd}$, $d_2^{nd}$ and $d_3^{nd}$) following a second generation of EM signals and the process may be repeated to receive three second fluorescence signals. Controller 110 may determine a phase shift between the first and second fluorescence signals following the generation of EM signals from each EM source. The controller may further correlate between each one of the three phase shifts to the corresponding change in distance (e.g., $d_1^{nd}$-$d_1^{st}$).

Accordingly, controller 110 may calculate the distance between EM source 130*a* and diamond 120*a* using, for example, the time difference between the generation of the EM signal from the source and the excitation of the corresponding first fluorescence signal. Alternatively, controller 110 may calculate the distance between EM sources 130*a* and diamond 120*a* by measuring the intensity of the fluorescence signal received in sensor 128*a* following the first fluorescence signal. Alternatively, controller 110 may calculate the distance between EM sources 130*a* and diamond 120*a* by measuring a phase shift between a fluorescence signal received following the current fluorescence signal and a fluorescence signal received following a previous fluorescence signal.

In some embodiments, the controller may calculate a second distance d2 between the diamond and the second EM radiation source based on the one or more second fluorescence signals in a similar way to the calculation of the first distance. In some embodiments, the controller may calculate a third distance d3 between the diamond and the third EM radiation source based the third fluorescence signal. In some embodiments, the second and/or third distances may be calculated using, time differences, fluorescence signal intensity measurements and/or phase shifts as disclosed above. In some embodiments, controller 110 may use more than one method for calculating the first, second and/or third distances. It should be appreciated that more than three EM sources may be used and accordingly more than three distances, intensities and/or phase shifts may be calculated in order to determine the location of the diamond and the medical device in a subject's body.

In some embodiments, the controller may calculate the position of the diamond based on the first and second distances and the fixed locations of the first and second EM sources. For example, knowing the locations of EM source 130*a* and 103*b* in a known plane, for example, the plane of the table carrying the subject, and the distances d1 and d2 of diamond 120 from each EM source, the location of the diamond in 2 dimensions can be calculated using triangulation. In order to add a third dimension to the position of diamond 120a in space, the fixed location of EM source 130c and the third distance d3 may be added to the calculation.

In some embodiments, the controller may be configured to calculate the position of the diamond based on the three first fluorescence signals and the three second fluorescence signals in the diamond, when actuator 122 activates NV centers in three different crystallographic orientation using three different MW frequencies. In some embodiments, controller 110 may be configured to determine a first vector extending between the diamond and first EM radiation source 130a based on the at least three first indications and the location of first EM radiation source 130a. In some embodiments, an EM signal having a known intensity may be generated from the first EM source. In some embodiments, during the emission of the first EM signal three different MW signals may be generated at three different times each having a frequency that us configured to activate NV centers at the known crystallographic direction. For example, a first MW frequency $f_1$ may generated by actuator 122 and may cause NV centers in the <111> direction to emit photons. The intensity of the emitted photons may be proportional to a portion of the intensity of the EM signal defined by the projection of the vector extending between the diamond and the first EM radiation source on the <111> direction in the cristal. The process may be repeated with MW frequencies $f_2$ and at least $f_3$ to receive three fluorescence signals having three intensities each corresponds to a different portion of the intensity of the EM signal defined by the projection of the vector extending between the diamond and the first EM radiation source on each crystallographic direction. The process may be repeated for second EM source 130b.

Accordingly, controller 110 may be configured to determine the first vector extending between the diamond and first EM radiation source 130a based on the at least three first indications and the fixed location of first EM radiation source 130a (e.g., the coordinates that were stored in a memory associated with controller 110). In some embodiments, controller 110 may be configured to determine a second vector extending between the diamond and second EM radiation source 130b based on the at least three second indications and the location of second EM radiation source 130b using the same methods. The first and second vectors may be defined in a coordinate system defined by the crystallographic directions of diamond 120a. In some embodiments, the fixed locations of EM sources 130a and 130b may be identified as points of the first and second vectors respectively, since the distance between the locations is fixed and known. In some embodiments, controller 110 may further calculate the position of the diamond as the intersection point of the first and second vectors.

Controller 110 may repeat the process in steps 205, 210, 215, 220, 225 and 230, multiple times, for example, 25 times per second, as in-vivo device 10 changes its position inside the subject's body. In some embodiments, the controller may display the location of diamond 120a on a screen visible to a user operating in-vivo device 10 to which diamond 120a is attached. For example, controller 110 may display the position of diamond 120a in a 3-dimensional simulation of the organ being operated, displayed on the screen, as discussed above.

Figure 3:
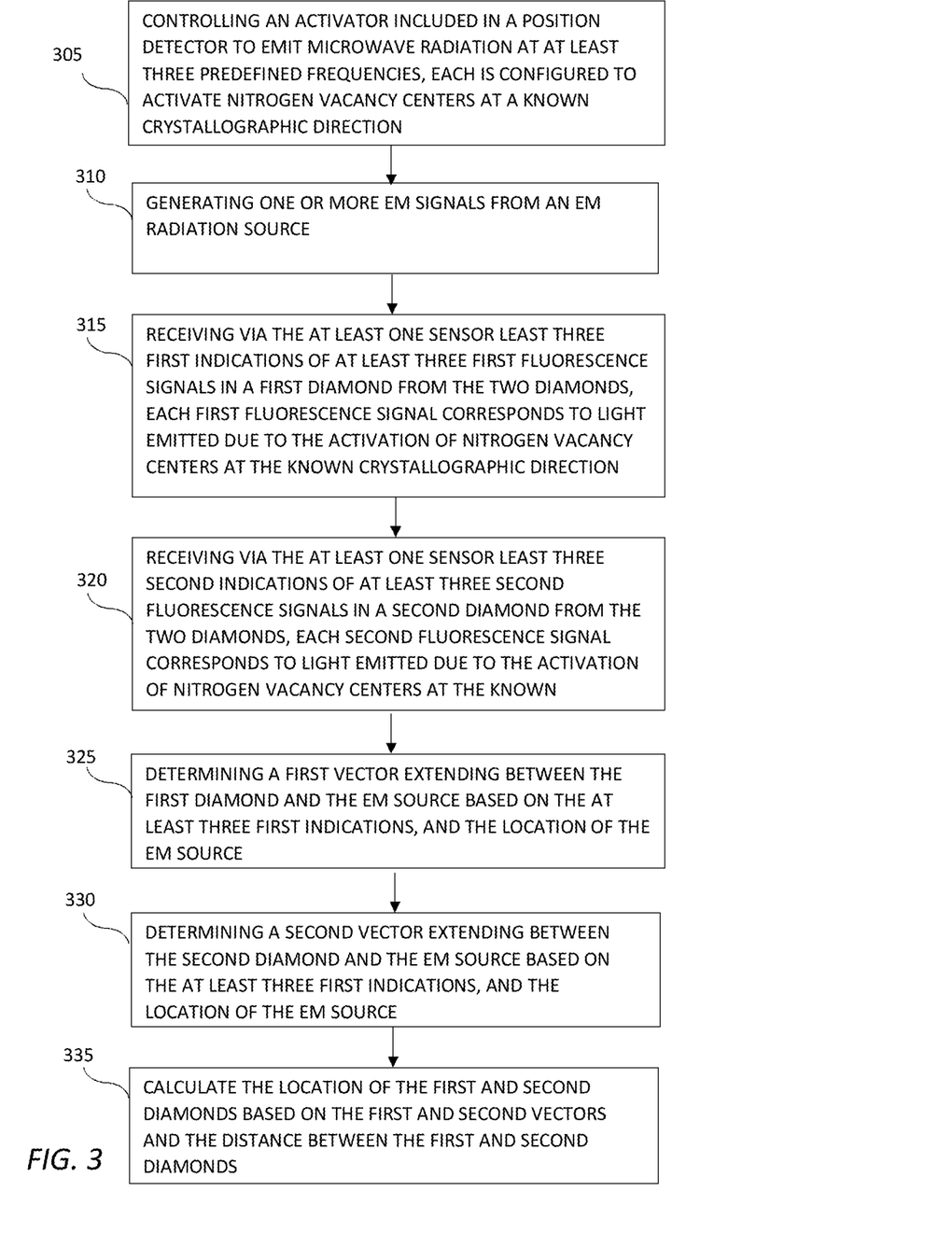
FIG. 3 is a flowchart of a method of controlling a position detector for in-vivo devices according to some embodiments of the invention.

Reference is now made to FIG. 3 which is a flowchart of a method of detecting a position of an in-vivo device according to some embodiments of the invention. The method of FIG. 3 may be performed by position detector 100 illustrated in FIG. 1C and controller 110. Such a position detector may include two diamonds 120a and 120b with nitrogen vacancy centers located at a known distance from each other, at least one sensor 128 and at least one activator 122 configured to activate the NV centers by emitting microwave radiation at at least three predefined frequencies, each may be configured to activate NV centers at a known crystallographic direction. The position detector may further include one electromagnetic (EM) radiation source 130 located in a fixed location and controller 110.

In some embodiments, controller 110 may be configured to control the at least one activator to emit microwave radiation at at least three predefined frequencies, each is configured to activate nitrogen vacancy centers at a known crystallographic direction in step 305. Each time at least one activator 122 emits MW radiation at one specific frequency the NV centers of the corresponding crystallographic orientation in at least one diamond or both diamonds 120a and 120b emit a fluorescence signal when exposed to one or more EM signals generated from EM source 130, in step 310.

The process of activating each crystallographic orientation using at least three specific MW frequencies while exposing diamonds 120a and 120b to the EM signal may continue for all specific MW frequencies. Therefore, controller 110 may be configured to receive, via the at least one sensor, least three first indications of at least three first fluorescence signals in a first diamond from the two diamonds, each first fluorescence signal corresponds to light emitted due to the activation of NV centers at the known crystallographic direction, in step 315. Controller 110 may further be configured to receive, via the at least one sensor, at least three second indications of at least three second fluorescence signals in a second diamond from the two diamonds, each second fluorescence signal corresponding to light emitted due to the activation of NV centers at the known crystallographic direction, in step 320.

In some embodiments, both diamonds 120a and 120b may be assembled such that the same crystallographic orientations in both diamonds will be in the same coordinate system and all crystallographic orientations are aligned. In some embodiments, controller 110 may be configured to calculate the vector defining the distance between diamond 120a and diamond 120b in the coordinate system defined by the diamonds crystallographic orientations.

In some embodiments, controller 110 may further be configured to determine a first vector extending between the first diamond and the EM source based on the at least three first indications, and the location of the EM source, in step 325. In some embodiments, controller 110 may further be configured to determine a second vector extending between the second diamond and the EM source based on the at least three second indications and the location of the EM source, in step 330. The controller may further calculate the location of the first and second diamonds based on the first and second vectors and the distance between the first and second diamonds, in step 335. The controller may first determine the vectors in the coordinate system defined by the diamonds crystallographic orientations and then project the coordinates of the diamond to a coordinate system of the space (e.g., room) accommodating detector 100.

In some embodiments, the location of diamonds 120a and 120b may be correlated to the location of an in-vivo device to which the diamonds are attached to and may presented to a user in the same why disclosed with respect to the method of FIG. 2.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A position detector for in-vivo devices, comprising:
a diamond with nitrogen vacancy centers;
an activator configured to activate the nitrogen vacancy centers in the diamond to emit fluorescence signals;
a sensor configured to detect the fluorescence signals emitted from the diamond;
two or more electromagnetic (EM) radiation sources located in fixed locations; and
a controller configured to control components of the position detector,
wherein the diamond and the sensor are attached to the in-vivo device in order to determine an in-vivo location of at least a portion of the medical device.

2. The position detector of claim 1, wherein the sensor includes a light guide connected to the diamond, wherein the light guide is configured to transmit the fluorescence signals from the diamond to a light detector.

3. The position detector of claim 1, wherein the sensor includes two electrodes placed at opposite sides of the diamond.

4. The position detector of claim 1, wherein the two or more EM radiation sources generate EM signals at a frequency range of 1-100 KHz.

5. The position detector of claim 1, wherein the EM radiation sources generate Direct Current (DC) or Alternating Current (AC) EM signals.

6. The position detector of claim 1, wherein the diamond comprises between 1 ppb –5000 ppm of nitrogen vacancy centers.

7. The position detector of claim 1, wherein the diamond is placed no more than 300 cm from the location of each of the EM radiation sources.

8. The position detector of claim 1, wherein the controller is configured to:
control the activator to activate the nitrogen vacancy centers in the diamond;
control a first EM radiation source of the two or more EM radiation sources to generate one or more EM signals;
receive via the sensor one or more first indications of one or more first fluorescence signals;
control a second EM radiation source of the two or more EM radiation sources to generate one or more EM signals;
receive via the sensor one or more second indications of one or more second fluorescence signals; and
calculate the position of the diamond based on the received indications.

9. The position detector of claim 8, further comprising:
a third radiation source located in a fixed location; and
wherein the controller is further configured to:
generate one or more EM signals from the third EM radiation source;
receive via the sensor one or more third indications of one or more third fluorescence signals in the diamond; and
calculate the position of the diamond further based on the received one or more third indications.

10. The position detector of claim 1, wherein the controller is further configured to:
control the activator to emit microwave radiation at at least three predefined frequencies, each is configured to activate nitrogen vacancy centers at a known crystallographic direction;
generate one or more EM signals from the first EM radiation source;
receive via the sensor at least three first indications of at least three first fluorescence signals in the diamond, each first fluorescence signal corresponding to light emitted due to the activation of nitrogen vacancy centers at the known crystallographic direction;
generate one or more EM signals from the second EM radiation source; and
receive via the sensor at least three second indications of at least three second fluorescence signals in the diamond, each second fluorescence signal corresponding to light emitted due to the activation of nitrogen vacancy centers at the known crystallographic direction;
and wherein calculating the position of the diamond comprises:
determining a first vector extending between the diamond and the first EM radiation source based on the at least three first indications and the location of the first EM radiation source;
determining a second vector extending between the diamond and the second EM radiation source based on the at least three second indications and the location of the second EM radiation source; and
calculating the position of the diamond as the intersection point of the first and second vectors.

11. A method of detecting a position of an in-vivo device, comprising:
controlling an activator included in a position detector, to activate nitrogen vacancy centers in a diamond, wherein the position detector further comprises:
the diamond with nitrogen vacancy centers;
a light guide connected to the diamond, passing optical signals from the diamond; and
two or more electromagnetic (EM) radiation sources located in known locations with respect to the diamond;
generating one or more EM signals from a first EM radiation source of the two or more EM radiation sources;
receiving via the light guide one or more first indications of one or more first fluorescence signals in the diamond;
generating one or more EM signals from a second EM radiation source of the two or more EM radiation sources;
receiving via the light guide one or more second indications of second fluorescence signals in the diamond; and
calculating the position of the diamond based on the received one or more indications.

12. The method of claim 11, further comprising:
generating one or more EM signals from a third EM radiation source included in the positioning detector, the third radiation source having known location, known direction, or both known location and known direction, with respect to the diamond;
receiving via the light guide one or more third indications of one or more third fluorescence signals in the diamond
calculating the position of the diamond further based on the received one or more third indications.

13. The method of claim 11, wherein calculating the position of the diamond comprises:
- calculating a first distance between the diamond and the first EM radiation source based on a time duration between the generation of the first EM signal and the first fluorescence signal; and
- calculating a second distance between the diamond and the second EM radiation source based on a time duration between the generation of the second EM signal and the second fluorescence signal.

14. The method of claim 13, further comprising:
calibrating the position detector by:
- placing the EM radiation sources in known distances from the diamond;
- generating EM signals from each EM radiation source;
- measuring time differences between the generation of each EM signal and a corresponding fluoresces signal; and
- correlating between known distances and the time differences.

15. The method of claim 11, further comprising:
receiving measurements of a first fluorescence intensity of the first the first fluorescence signal and a second fluorescence intensity of the second fluorescence signal;
and wherein calculating the position of the diamond comprises:
calculating a first distance between the diamond and the first EM radiation source based on the first fluorescence intensity; and
calculating a second distance between the diamond and the second EM radiation source based on the second fluorescence intensity.

16. The method of claim 15, further comprising:
calibrating the position detector by:
- placing the EM radiation sources in known distances from the diamond;
- generating EM signals from each EM radiation source;
- measuring an intensity of a fluorescence signal for each EM signals; and
- associating the intensity of a fluorescence signal with a known distance.

17. The method of claim 11, further comprising:
- receiving a first fluorescence signal and a second fluorescence signal when the diamond is in a first position;
- receiving a first fluorescence signal and a second fluorescence signal when the diamond is in a second position;
- calculating a first phase shift between the first fluorescence signals received at when diamond is in the first and second positions; and
- calculating a second phase shift between the second fluorescence signals received at when diamond is in the first and second positions;
and wherein calculating the position of the diamond comprises:
calculating a first distance based on the first phase shift and a second distance based on the second phase shift.

18. The method of claim 17, further comprising:
calibrating the position detector by:
- placing the first EM radiation source at a first known distance from the diamond and the second EM radiation source at a second known distance from the diamond;
- generating a first EM signal from the first EM radiation source and a second EM signal from the second EM source;
- placing the first EM radiation source at a third known distance from the diamond and the second EM radiation source at a fourth known distance from the diamond;
- generating a third EM signal from the first EM radiation source and a fourth EM signal from the second EM source;
- calculating a first phase shift between the first and third fluorescence signals;
- calculating a second phase shift between the second and fourth fluorescence signals;
- correlating between the first phase shift and a change between the first and third distances; and
- correlating between the second phase shift and a change between the second and fourth distances.

19. The method of claim 11, wherein the activator is a microwave radiation source configured to emit microwave radiation at one of more frequencies and the method further comprising:
- controlling the activator to emit microwave radiation at at least three predefined frequencies, each is configured to activate nitrogen vacancy centers at a known crystallographic direction;
- generating one or more EM signals from the first EM radiation source;
- receiving via the light guide at least three first indications of at least three first fluorescence signals in the diamond, each first fluorescence signal corresponds to light emitted due to the activation of nitrogen vacancy centers at the known crystallographic direction;
- generating one or more EM signals from the second EM radiation source; and
- receiving via the light guide at least three second indications of at least three second fluorescence signals in the diamond, each second fluorescence signal corresponds to light emitted due to the activation of nitrogen vacancy centers at the known crystallographic direction,
and wherein calculating the position of the diamond comprises:
- determining a first vector extending between the diamond and the first EM source based on the at least three first indications and the location of the first EM source;
- determining a second vector extending between the diamond and the first EM source based on the at least three second indications and the location of the second EM source; and
- calculating the position of the diamond as the intersection point of the first and second vectors.

* * * * *